United States Patent

Herold et al.

[11] Patent Number: 5,249,862
[45] Date of Patent: Oct. 5, 1993

[54] DYNAMIC MIXER

[75] Inventors: Wolf D. Herold, Seefeld; Gerd Brandhorst, Munich; Guenter Rehfeld, Diessen, all of Fed. Rep. of Germany

[73] Assignee: THERA Patent GmbH & Co.KG Gesellschaft fur industrielle Schutzrechte, Seefeld, Fed. Rep. of Germany

[21] Appl. No.: 811,438

[22] Filed: Dec. 23, 1991

[30] Foreign Application Priority Data

Dec. 21, 1990 [DE] Fed. Rep. of Germany ... 9017323[U]

[51] Int. Cl.$^5$ ................................................ B01F 7/00
[52] U.S. Cl. ...................................... 366/312; 222/137; 222/145
[58] Field of Search ............... 222/135, 145, 136, 137; 366/155, 156, 165, 266, 309, 310, 325, 279, 312

[56] References Cited

U.S. PATENT DOCUMENTS

| | | | |
|---|---|---|---|
| 3,067,987 | 12/1962 | Ballou et al. | 222/145 X |
| 3,570,719 | 3/1971 | Schiff | 222/137 |
| 3,767,085 | 10/1973 | Cannon et al. | 222/82 |
| 3,949,904 | 4/1976 | Hendrickson | 222/145 X |
| 4,107,793 | 8/1978 | Wallace | 366/312 |
| 4,432,469 | 2/1984 | Eble et al. | 222/137 X |
| 4,767,025 | 8/1988 | Gebauer et al. | 222/145 X |
| 4,793,151 | 12/1988 | Masel et al. | 366/312 X |
| 4,881,821 | 11/1989 | Stutz | 222/145 X |
| 4,934,827 | 6/1990 | Taschke et al. | 222/137 X |
| 4,951,843 | 8/1990 | Paetow | 222/145 |
| 5,005,735 | 4/1991 | Keller | 222/137 |

FOREIGN PATENT DOCUMENTS

| | | | |
|---|---|---|---|
| 0087029 | 8/1983 | European Pat. Off. | |
| 3635635.2 | 4/1988 | Fed. Rep. of Germany. | |
| 8717424.3 | 12/1988 | Fed. Rep. of Germany. | |
| 3723677 | 1/1989 | Fed. Rep. of Germany | 366/156 |
| 393270 | 11/1961 | Switzerland | 366/7 |
| 674717 | 7/1990 | Switzerland | 366/156 |
| 8706852 | 11/1987 | World Int. Prop. O. | 366/312 |

Primary Examiner—Andres Kashnikow
Assistant Examiner—Kenneth DeRosa
Attorney, Agent, or Firm—Foley & Lardner

[57] ABSTRACT

A dynamic mixer comprises a cylindrical chamber portion 50 the rear end of which is closed by a sealing plate 51 provided with conical pipe sockets 58, 59 adapted for being directly inserted into outlet openings of cartridges from which the pasty components to be mixed are supplied. Due to the closed structure of the mixer housing 50, 51, contamination of the device by the components and cross-contamination between them is avoided when the mixer is removed from the cartridges. Further, the direct connection of the mixer to the cartridges results in minimum travelling distances for the components, thus low friction losses, which is particularly advantageous in case of substances of high-viscosity.

4 Claims, 1 Drawing Sheet

DYNAMIC MIXER

BACKGROUND OF THE INVENTION

This invention relates to a dynamic mixer which comprises a housing including a substantially cylindrical chamber portion defining a longitudinal axis and having at its rear end inlet means adapted for connection to supply means containing the components to be mixed, and at its front end a discharge opening for the mixture, and a mixer element disposed within the chamber portion for rotation about the longitudinal axis.

A mixer of this type is known from DE-U-8,717,424. In the known device, the chamber portion of the housing enclosing the rotary mixer element has its rear end sealed by a cap provided with openings through which hoses may be inserted. The components to be mixed are supplied via the hoses from supply cartridges, out of which the substances may be discharged by pistons. The use of hoses is possible with substances of limited viscosity only.

In a further mixer known from EP-A-0 087 029, a massive connecting piece is provided with supply bores for connection to cartridges. While this construction is suitable for materials of high viscosity also, substantial friction will occur in the supply bores of the connecting piece, so that a propelling device of correspondingly sturdy design is required for discharging the components from the cartridges.

In a further dynamic mixer known from DE-A-3,635,635, the housing is rearwardly open and fastened via a bayonet-type connector to a holder which is provided with separate supply channels for the components. In this device, there is a danger of contamination by, and cross-contamination between, the components when the mixer is exchanged, particularly in case of stringy substances. This may result in material hardening in a part of the device which is not replaced together with the mixer.

SUMMARY OF THE INVENTION

It is an object of the invention to provide a dynamic mixer which is exchanged by simple handling without the danger of spreading or cross-contamination of the components that are to be mixed. It is a further object of the invention to devise a dynamic mixer which permits the components to be supplied with minimum friction loss.

These objects are met in accordance with the invention by a dynamic mixer comprising a housing including a substantially cylindrical chamber portion defining a longitudinal axis and having at its rear end inlet means adapted for connection to supply means containing the components to be mixed, and at its front end a discharge opening for the mixture, and a mixer element disposed within the chamber portion for rotation about the longitudinal axis, wherein the housing includes at the rear end of the chamber portion a sealing member with rearwardly projecting pipe means adapted for direct introduction into outlet openings of the supply means.

In the mixer according to the present invention, the sealing member which confines the rear end of the chamber portion of the mixer housing permits the rearwardly projecting pipe means to be directly introduced into corresponding outlet openings of the supply means which contain the components. The travelling distance of the components from the supply means to the mixer element, thus the friction losses, are thereby reduced to a minimum.

At the same time, the mixer is formed as a closed structural part with distinctly separated component supply paths and may therefore be removed from the supply means and replaced by a fresh mixer without the danger of spreading or cross-contamination of the components. In case of components which react chemically with each other, such as dental molding materials or adhesives, exchanging of the mixer is required upon each prolonged interruption of the mixing and discharging process as the mass will harden within the mixer and render the same inoperable.

In a preferred embodiment, the outer surfaces of the pipe means are conical to provide an efficient seal with respect to the outlet openings of the supply means.

In order to simplify the manufacture and assembly of the mixer, the sealing means is preferably adapted to be inserted from the rear into a radial flange portion of the housing. This feature is significant because the mixer is advantageously formed as an inexpensive disposable part.

In another preferred embodiment, the flange portion has a forwardly facing outer surface for engagement with a holder that connects the mixer to the supply means. With this concept, connecting the mixer to the supply means will simultaneously seal the pipe means with respect to the outlet openings of the supply means, and the sealing means with respect to the housing.

According to a further advantageous embodiment, the sealing member has a bore for rotatably supporting a rear end of the mixer element, the mixer element including wiper means having leading blade means for wiping the interior surface of the sealing member upon rotation of the mixer element. While a wiper element for cutting up the component strands as they are supplied is known per se from DE-A-3,635,635, the cooperation of such a wiper element with the sealing plate provided by the invention results in an unambiguous spatial relationship between these elements as is significant for a proper wiping action.

DETAILED DESCRIPTION OF A PREFERRED EMBODIMENT

Figure 1:
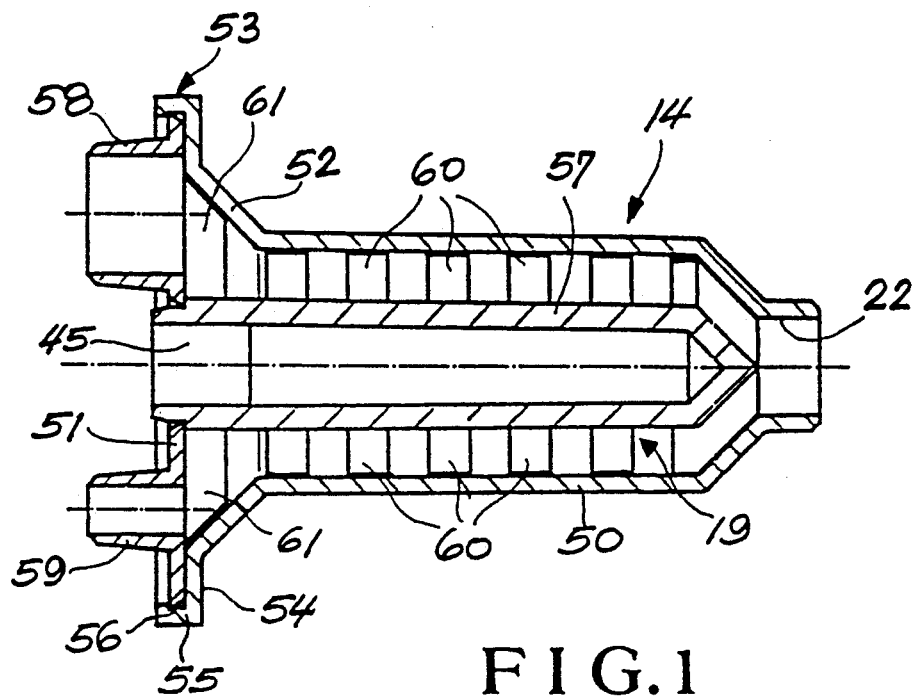
FIG. 1 shows an axial section through a mixer.

The mixer identified by numeral 14 in FIG. 1 consists of three molded synthetic resin parts, namely a housing chamber portion 50 which is cylindrical throughout its principle part and is provided with a discharge opening 22; a sealing plate 51 which forms the rear wall of the housing; and a mixer element 19 supported within the housing for rotation about the longitudinal axis of the chamber portion 50.

At the end remote from the discharge opening 22, the chamber portion 50 has a rearwardly enlarged conical portion 52 which terminates in a radially outwardly extending flange portion 53. The flange portion 53 provides an outer surface 54 facing forwardly (i.e. towards the discharge opening 22). The cylindrical part 55 of the flange portion 53 is internally provided with a radial groove 56.

The sealing plate 51 is so dimensioned that it can be inserted from the rear into the flange portion 53 and snapped into the radial groove 56 by resilient deformation of the material of the housing. A seal is thereby achieved between the chamber portion 50 and the sealing plate 51.

The sealing plate 51 is further provided with a central bore in which the hollow core 57 of the mixer element 19 is rotatably supported. The end of the core 57 extends through the plate 51 and has a hexagonal recess 45 for engagement by the complementarily formed end of a drive shaft (not shown).

Two rearwardly projecting pipe sockets 58, 59 are integrally formed with the sealing plate 51 at positions oppositely offset from the center bore. The pipe sockets 58, 59 are adapted for being directly inserted into outlet openings of cartridges 12, 13 (shown in FIG. 2) which contain the components to be mixed. The outer surfaces of the pipe sockets 58, 59 are conically formed with a rearward tapering to provide a seal between the pipe sockets 58, 59 and the outlet openings of the cartridges 12, 13.

In FIG. 1, the pipe sockets 58, 59 are shown with different internal cross-sections to illustrate a case in which the two components are to be mixed at a ratio different from 1:1.

The mixer element 19 carries a group of mixer blades 60 integrally formed on the outer surface of the core 57. The blades 60 are provided within the cylindrical portion of the chamber portion 50 and end short of the internal chamber wall.

A plurality of wiper arms 61 are integrally formed at the rear end of the hollow core 57, each wiper arm being formed with a cutting edge at the side which leads when the mixer element 19 rotates. Starting from the cutting edge, each wiper arm 61 forms a forwardly rising inclined surface which assists in moving of the components in the discharging direction.

The cutting edges engage the inner surface of the sealing plate 51 and serve to cut up the component strands as they enter the mixer housing via the pipe sockets 58, 59. The fact that the strands are immediately wiped off and cut up is advantageous because it guarantees a clean severing of the component strands in virtually any position, when the mixer 14 is removed from the cartridges 12, 13.

Figure 2:
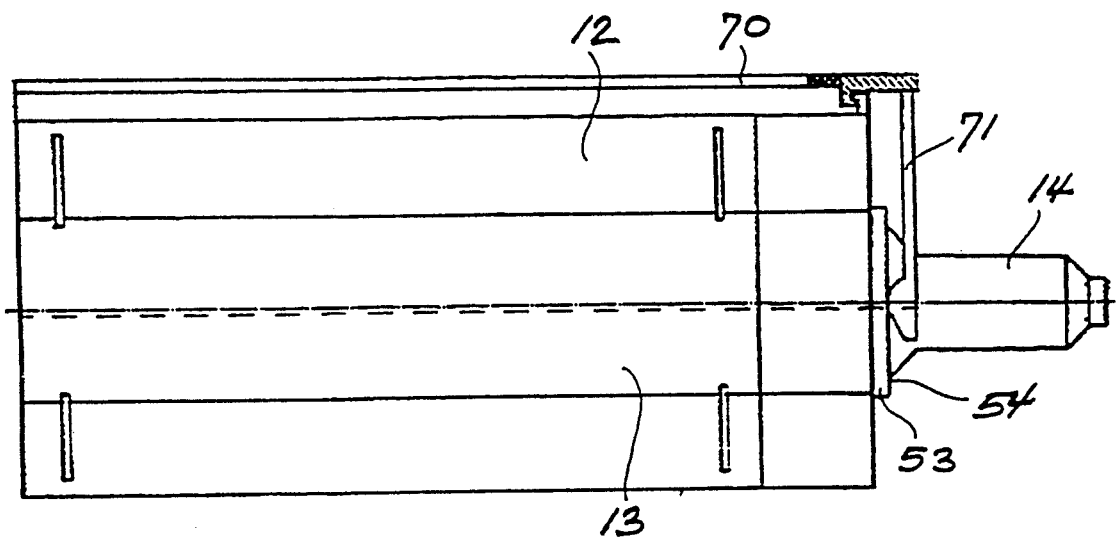
FIG. 2 is a side view of a cartridge assembly with the mixer of FIG. 1 being connected to the right-hand end thereof.

FIG. 2 shows the mixer 14 in a position mounted at the front end of a cartridge unit comprising two cartridges 12, 13. The mixer 14 is held in position by a fork-shaped retainer 71 provided at the front end of a lid 70 of the cartridge unit.

In the closed position of the lid shown in FIG. 2, the two fingers of the retainer 71 bear against the front surface 54 of the flange portion 53 of the mixer 14 at two diametrically opposite locations to cause a resilient bias of the mixer 14 towards the cartridges 12, 13. Due to this biassing action, the conical pipe sockets 58, 59 are sealingly pressed into the outlet openings (not shown) of the cartridges, and similarly the sealing plate 51 is sealingly urged against the inner surface of the flange portion 53.

What is claimed is:

1. A dynamic mixer comprising:
   a housing including a substantially cylindrical chamber portion defining a longitudinal axis and having front and rear ends,
   a sealing member for closing the rear end of said chamber portion, said sealing member having an interior surface, a central bore, and rearwardly projecting pipe means adapted for direct introduction into outlet openings of supply means containing components to be mixed,
   a discharge opening provided at the front end of said chamber portion for discharging a mixture formed from said components, and
   a mixer element disposed within said chamber portion and supported by said central bore for rotation about said longitudinal axis, said mixer element including wiper means for wiping the interior surface of said sealing member when said mixer element rotates, said wiper means having leading cutting edges for cutting up strands of said components as they enter said housing.

2. The mixer of claim 1, wherein said pipe means have rearwardly tapered outer surfaces.

3. The mixer of claim 1, including a radial flange portion formed on said chamber portion, and wherein said sealing member is adapted to be inserted from the rear into said flange portion.

4. The mixer of claim 3, wherein said flange portion has a forwardly facing outer surface adapted for engagement by holding means connecting said mixer to said supply means.

* * * * *